(12) United States Patent  
Shinozaki

(10) Patent No.: US 12,239,414 B2  
(45) Date of Patent: Mar. 4, 2025

(54) DERMOSCOPE, DERMOSCOPE ADAPTER, AND PROGRAM

(71) Applicant: Derma Medical Inc., Yokohama (JP)

(72) Inventor: Takashi Shinozaki, Yokohama (JP)

(73) Assignee: Derma Medical Inc., Yokohama (JP)

( * ) Notice: Subject to any disclaimer, the term of this patent is extended or adjusted under 35 U.S.C. 154(b) by 0 days.

(21) Appl. No.: 17/927,308

(22) PCT Filed: Jul. 2, 2021

(86) PCT No.: PCT/JP2021/025118  
§ 371 (c)(1),  
(2) Date: Nov. 22, 2022

(87) PCT Pub. No.: WO2022/130667  
PCT Pub. Date: Jun. 23, 2022

(65) Prior Publication Data  
US 2023/0190108 A1    Jun. 22, 2023

(30) Foreign Application Priority Data  
Dec. 15, 2020    (JP) ................. 2020-207742

(51) Int. Cl.  
*A61B 5/00* (2006.01)  
*G02B 27/28* (2006.01)  
(Continued)

(52) U.S. Cl.  
CPC .......... *A61B 5/0077* (2013.01); *A61B 5/0013* (2013.01); *A61B 5/0022* (2013.01); (Continued)

(58) Field of Classification Search  
CPC ..... A61B 10/00; A61B 5/0013; A61B 5/0022; A61B 5/0077; A61B 5/441; A61B 5/444; (Continued)

(56) References Cited

U.S. PATENT DOCUMENTS

2018/0140196 A1    5/2018    Simchi et al.

FOREIGN PATENT DOCUMENTS

| JP | 2005-192944 A | 7/2005 |
|---|---|---|
| JP | 2009-011824 A | 1/2009 |

(Continued)

OTHER PUBLICATIONS

International Search Report received in International Application No. PCT/JP2021/025118, mailed Sep. 7, 2021, in 51 pages.

*Primary Examiner* — Mark D Remaly  
(74) *Attorney, Agent, or Firm* — Knobbe, Martens, Olson & Bear, LLP

(57) ABSTRACT

Provided is an application program (app) for functioning a dermoscope, a dermoscope adapter, and a smartphone as a dermoscope. A dermoscope 100 for observing skin tissue according to the present invention includes a smartphone 110 including a camera 111 and a photoflash 107 and being communicable, and being capable of instructing from a graphical user interface displayed on a liquid crystal display; a case 101 containing the smartphone 110 and including a base member 103 fixed on a side opposite to a liquid crystal display to operate the smartphone 110; and an observation adaptor 102 detachably retained on the base member 103; wherein the camera 111 performs photographing through a first circular polarization filter 106; wherein the base member 103 movably retains a second circular polarization filter 108 for leading a polarization state of LED light emitted by the photoflash 107 to form circularly polarized light.

10 Claims, 14 Drawing Sheets

(51) Int. Cl.
    *G03B 15/05*     (2021.01)
    *G03B 17/56*     (2021.01)
    *H04N 23/53*     (2023.01)
    *H04N 23/55*     (2023.01)
    *H04N 23/56*     (2023.01)
    *H04N 23/63*     (2023.01)

(52) U.S. Cl.
    CPC ............ *A61B 5/441* (2013.01); *G02B 27/288* (2013.01); *G03B 15/05* (2013.01); *G03B 17/565* (2013.01); *H04N 23/53* (2023.01); *H04N 23/55* (2023.01); *H04N 23/56* (2023.01); *H04N 23/631* (2023.01); *G03B 2215/0567* (2013.01); *G03B 2215/0592* (2013.01)

(58) Field of Classification Search
    CPC ...... A61B 5/6898; H04N 23/53; H04N 23/55; H04N 23/555; H04N 23/56; H04N 23/631; G02B 27/288; G03B 15/05; G03B 17/565; G03B 2215/0567; G03B 2215/0592
    See application file for complete search history.

(56) References Cited

FOREIGN PATENT DOCUMENTS

| | | |
|---|---|---|
| JP | 2016-530917 A | 10/2016 |
| JP | 2018-163240 A | 10/2018 |
| JP | 2019-115648 A | 7/2019 |
| JP | 2019-117278 A | 7/2019 |

Fig. 7
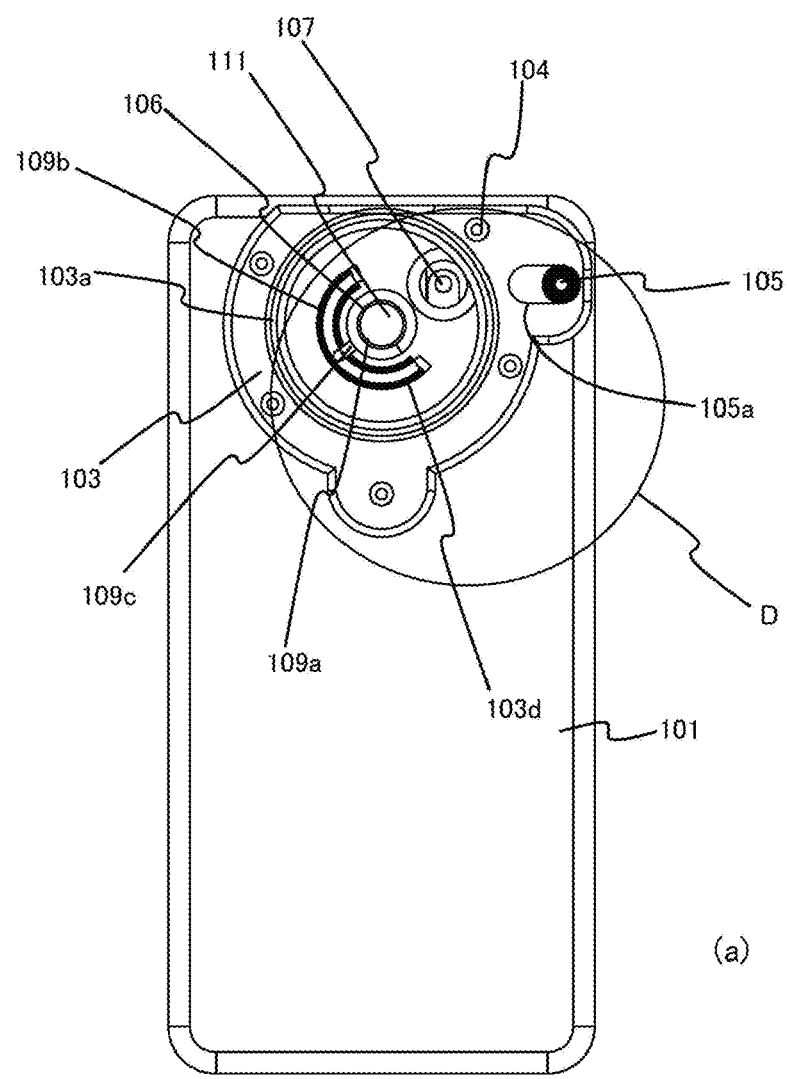
(a)
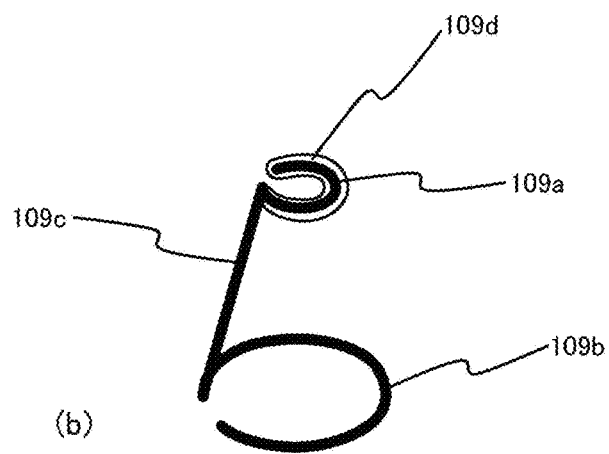
(b)

*Fig. 14*
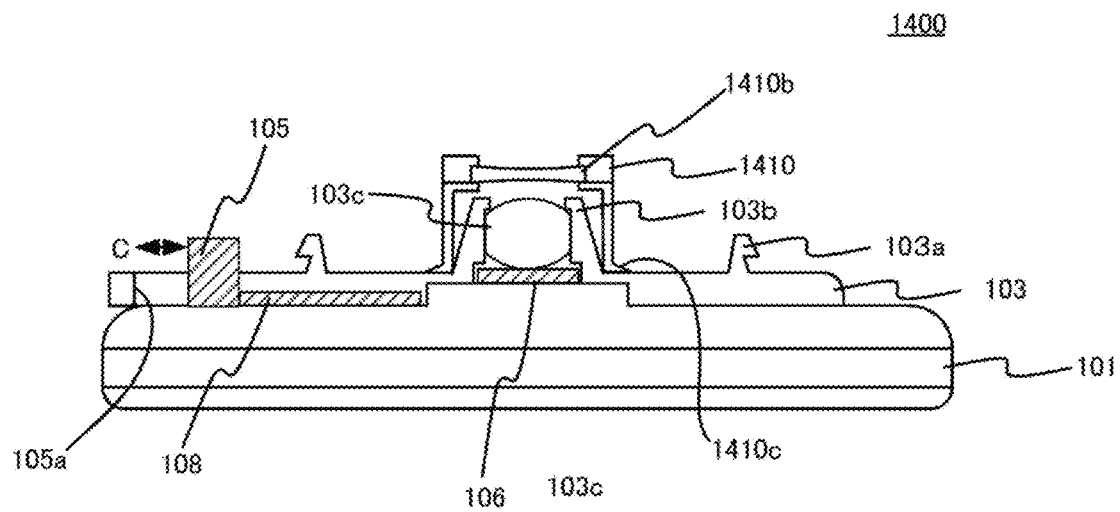
(a)
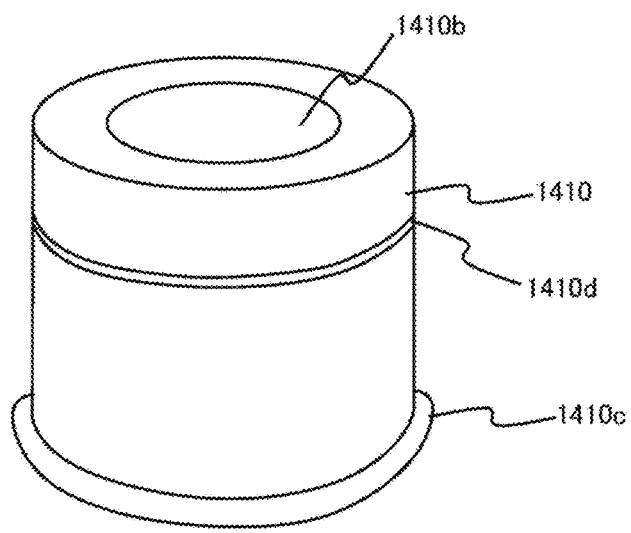
(b)

DERMOSCOPE, DERMOSCOPE ADAPTER, AND PROGRAM

TECHNICAL FIELD

The present invention relates to a dermoscope, a dermoscope adapter, and an application program (app) for making a smartphone functioned as a dermoscope.

BACKGROUND ART

Conventionally, there has been several known examination devices and examination methods to examine pigmentation having a specified size by a digital camera. Such devices are referred to as a dermoscope, and in addition to use for skin surface, they can be used in a combination with a polarization filter, thereby examining pigmentation condition and other lesions of not only skin surface but also skin tissue leading to dermis.

Dermoscopes are capable of checking a lesion on superficial tissue, but as for more detailed examination of a lesion, doctors or other professionals may intend to further magnify an affected area or a region suspected as an affected area to determine a condition of a capillary vessel in the region. However, conventional dermoscopes has been made as devices separated from a photographing function and can also be upsized due to addition of lighting and a camera in photographing, and thus has had limited availability. Furthermore, due to absence of a camera function, there has been inconvenience such as less recordability of images or incapability of direct supply for AI image determination or the like.

The Applicant has previously developed a digital dermoscope that enables high-accuracy examination, and proposed a digital dermoscope using a circular polarization filter as described in e.g., PCT/JP2018/000204 (Patent Literature 1), Japanese Patent Specification No. 6705957 (Patent Literature 2), US2019159678 A1 (Patent Literature 3, issued), EP3431011 A1 (Patent Literature 4), and CN109475352A (Patent Literature 5).

The digital dermoscope described in Patent Literature 1 is functioned as a dermoscope by applying a dedicated adapter to a digital camera and separating reflections from the skin surface and the inner skin with use of an optical isolator function, thereby performing observation.

Although digital cameras have been conventionally used, smartphone-mounted cameras of recent years are also digital cameras, some of which has further appeared with a higher resolution relative to dedicated cameras. Moreover, in spite of originally being telephones, smartphones have developed as information processing apparatuses having both an imaging function and an information processing function: this suggests availability apart from imaging means having only a camera-dedicated function such as digital cameras, and leads to thinking of enabling provision of more sophisticated digital dermoscope.

A dermoscope using a smartphone has been known in e.g., Non-patent Literature 1 (https://fcaresystems.com/products/phlebology/dermalite-dl1 (Jul. 16, 2020)). In the dermoscope described in Non-patent Literature 1, an attachment is attached to a smartphone, thereby enabling polariscopy using cross-Nicol arrangement. However, there have been faults such as that a dermoscope must be removed from an affected area during change of polarization filters, thus preventing polariscopy in the same visual field; and furthermore, that a high-intensity illumination light source is required because of polariscopy being performed with use of cross-Nicol arrangement, thus leading to increased weight. Furthermore, JP2014-180285 (Patent Literature 6) discloses a dermoscope for observing the skin by using two polarization filters. Although patent Literature 6 also enables to observe the skin, a large lens module should be connected to the smartphone and for switching polarization states, positionings of LEDs should be changed. Thus, if the polarization states are changed, light source positionings change accordingly such that lesions observation under the same lighting can not be performed.

CITATION LIST

Patent Literature

1. PCT/JP2018/000294
2. Japanese Patent No. 6705957
3. US2019159678 A1 Specification
4. EP3431011 A1 Specification
5. CN109475352 A Specification
6. JP2014-180285

Non-Patent Literature 1. https://fcaresystems.com/products/phlebology/dermalite-dl1 (Jul. 16, 2020)

SUMMARY OF INVENTION

The present invention was made in view of the conventional technologies described above, and the present invention has an object to provide a dermoscope using a smartphone.

An embodiment of the present invention provides:
a dermoscope for observing skin tissue, the dermoscope including:
a smartphone including a camera and a photoflash and being communicable, and being capable of instructing from a graphical user interface displayed on a liquid crystal display,
a case containing the smartphone and including a base member fixed on a side opposite to the liquid crystal display to operate the smartphone, and
an observation adaptor detachably retained on the base member,
wherein the camera performs photographing through a first circular polarization filter, and
wherein the base member movably retains a second circular polarization filter for leading a polarization state of LED light emitted by the photoflash to form circularly polarized light.

In the embodiment, the dermoscope comprises a slider knob for adjusting the position of the second circular polarization filter, wherein the slider knob is movably retained along a long hole formed in the base member, and wherein the second circular polarization filter is fixed to the slider knob.

In the embodiment, the smartphone enables to display an image of the skin tissue and a scale for measuring a size of an affected area of the skin tissue on a liquid crystal display.

In the embodiment, the dermoscope comprises a narrow-area observation adaptor, the narrow-area observation adaptor comprising a stand member including a supportive ring, a base part positioned around a periphery of the camera, and a supportive rod extending between the supportive ring and the base part, wherein the narrow-area observation adaptor is detachable to the base member.

In the embodiment, the dermoscope enables to equip an observation adaptor having a truncated-cone shape for observing the skin tissue.

Furthermore, in another aspect, provided is a dermoscope adapter including a camera and a photoflash and being communicable, and for making a smartphone functioned as a dermoscope, the smartphone being capable of instructing from a graphical user interface displayed on a liquid crystal display, the dermoscope adapter including:

a case including a space capable of containing a smartphone, a base member fixed on the case and having formation of a circular hook for retaining an observation adaptor, and the dermoscope adapter containing:

a first circular polarization filter arranged over the camera, and a second circular polarization filter attached to a slider knob movably retained along a long hole formed in the base member, the second circular polarization filter being to extend to the position of the photoflash along with movement of the slider knob.

In the embodiment, the base member allows equipment of an observation adaptor for observing the skin tissue or a narrow-area observation adaptor for observing a narrow affected area.

Furthermore, in another aspect, provided is an application program including a camera and photoflash and being communicable, and for making a smartphone functioned as the dermoscope described above, the smartphone being capable of instructing from a graphical user interface displayed on a liquid crystal display, the application program making the smartphone functioned as:

means adapted to make a setting for providing a function as a dermoscope in response to activation of the application program, means adapted to store the setting as setting data in a nonvolatile memory of the smartphone, and means adapted to drive the camera of the smartphone base on the setting data, and adapted to perform at least one function of observation, photographing, and image saving of a skin affected area.

In the embodiment, the smartphone is further functioned as means adapted to send via internet the image taken by the camera and performing remote diagnosis.

In the embodiment, the application program functions the smartphone to display an image of the skin tissue and a scale for measuring a size of an affected area of the skin tissue on a liquid crystal display.

The present invention allows utilization of a smartphone as a digital dermoscope and provides improved efficiency in dermatological diagnosis.

BRIEF DESCRIPTION OF DRAWINGS

FIG. 7 shows a front view with removing an observation adaptor 102 in the second embodiment 600 of the dermoscope 100 shown in FIG. 6.

FIG. 14 shows shows a drawing illustrating an embodiment 1400 equipping a wide area photographing adaptor 1410 for photographing the wider area.

EMBODIMENTS PRACTICING INVENTION

Figure 1:
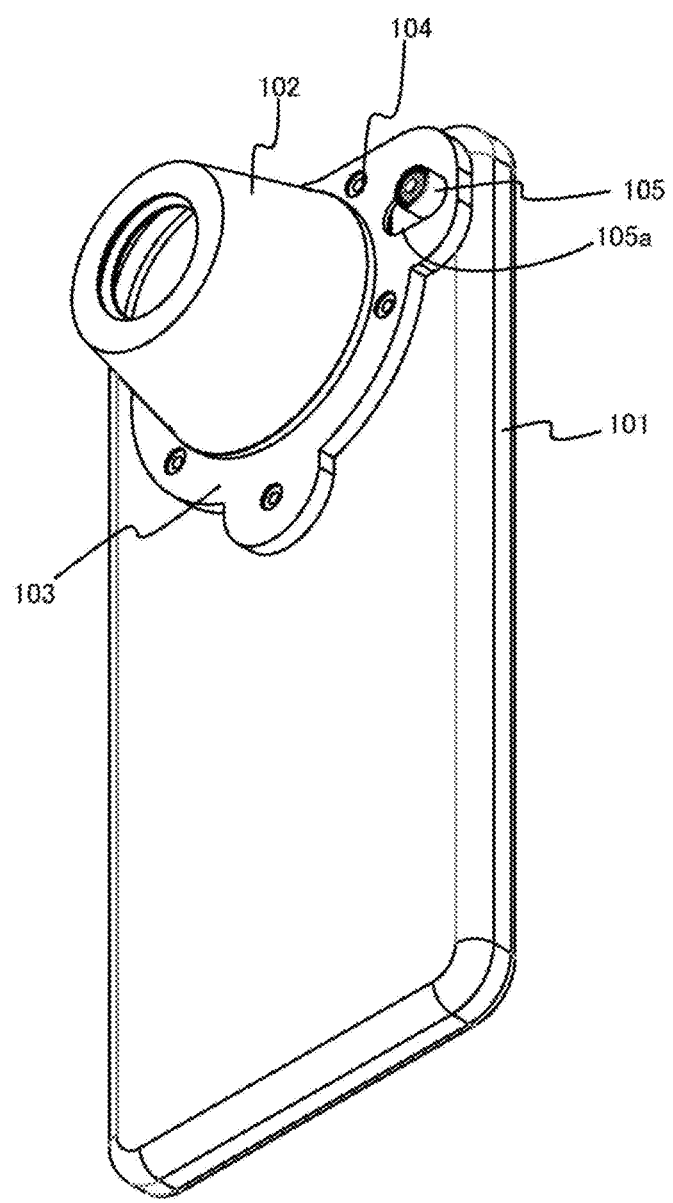
FIG. 1 shows a perspective view of a dermoscope 100 of the embodiment.

The present invention will now be described with embodiments, but the present invention is not limited to the embodiments described later. FIG. 1 shows a perspective view of a dermoscope 100 of the embodiment. The dermoscope 100 of the embodiment includes a smartphone, a case 101 containing the smartphone, a base member 103 detachably fixed on the case 101, and an observation adaptor 102 detachably applied to the base member 103. In FIG. 1, the smartphone is received in a receptacle part formed opposite to the base member 103 and a liquid crystal display of the smartphone is exposed opposite to the side where the base member 103 is disposed to enable operation and image observation by a user.

The case 101 receiving a smartphone and the base member 103 detachably fixed on the case 101 configures an observation adaptor 102. In use of the observation adaptor 102, a lightguide, and the like, a length with addition of the length of the lightguide is set as a dimension for arranging a camera of the smartphone at the distance for a close-up lens to come into focus as described later, allowing observation of a focused image in close-up. Observation is provided by a liquid crystal display equipped in a smartphone, thus allowing even in an image enlarged. This eliminates the need for a user (such as a doctor) to observe with his/her face close to an affected area or a dermoscope as conventional observation in a lens-type dermoscopy and facilitates observation. In other words, the dermoscope 100 of the embodiment can be said as a new dermoscope having both characteristics of two kinds of dermoscopes such as a magnifying glass type and a digital camera type.

The smartphone is not particularly limited to, for example, iPhone® manufactured by Apple, a smartphone manufactured by Xiaomi, a smartphone manufactured by Sharp, a smartphone manufactured by Sony, a smartphone manufactured by Samsung, a smartphone manufactured by Huawei, a smartphone manufactured by OPPO, a smartphone manufactured by ASUS, a smartphone manufactured by Fujitsu, a smartphone manufactured by Google, a smartphone manufactured by LG or RAICA.

The smartphone carries a CPU such as Snapdragon®, includes RAM, ROM, a flash memory, a memory card, various interfaces, a camera, and a photoflash, executes various programs, e.g., a program referred to as an app, under an operating system (OS) such as iOS®, Android®, XPERIA®, and CHROME®, and is allowed for information communication via internet by Wi-Fi, 4G, 5G or a further next-generation communication standard, Bluetooth®, Ethernet®, or the like.

Additionally, in the embodiment, although a telephone function of the smartphone is not essential, a SIM card may be implemented thereby performing telephone communication. Moreover, the smartphone of the embodiment is used, in which the position of a built-in camera is arranged at the top center of the smartphone in view of operability, but the position of the built-in camera may be the top right end or the top left end. Moreover, although resolution is not also particularly limited, it is preferable to use a smartphone having a resolution of 20 million pixels or more: for example, a smartphone mounted with a built-in camera having a resolution of 64 million pixels can be used.

The case 101 contains a smartphone and may have any shape and quality of material as long as it can securely retain a smartphone. In view of handleability, retentivity, and the like of the dermoscope 100, a case can be used having a shape covering a part other than a display of the smartphone, a camera, a photoflash, and the like of the smartphone. Additionally, material of the case 101 has no limitation in quality of material such as polycarbonate or silicone, as long as it is material having strength to an extent capable of fixing the base member 103.

In the embodiment, the base member 103 is fixed to the case 101 using a screw 104, the observation adaptor 102 is detachably applied on the side opposite to the case 101 of the base member 103. Furthermore, a first circular polarization filter covering a built-in camera of the smartphone is applied in the vicinity of the smartphone of the base member 103.

The observation adaptor 102 is a part to contact with an affected area and is made of silicone rubber so as to have an appropriate flexibility and to be also capable of undergoing sterilization, and has a generally truncated cone shape, in which the bottom face of the truncated cone is retained on the base member 103 and the top face includes an optically transparent protection member applied thereon.

At a part close to a photoflash of the base member 103, a slider knob 105 is arranged, which slidably retains a circular polarization filter (not shown). The slider knob 105 has a second circular polarization filter fixed in the vicinity of the case 101. The slider knob 105 is contained in a long hole 105a containing the slider knob 105. Once the slider knob 105 is slid in the major axis direction of the long hole 105a, the second circular polarization filter, which is fixed to the slider knob 105, extends to the position of the photoflash and covers this, and converts LED light emitted from the photoflash into circularly polarized light, and then irradiates the circular polarization on an affected area. Meanwhile, once a user moves the second circular polarization filter to a position not covering the photoflash, unpolarized LED light from the photoflash is irradiated onto an affected area, allowing observation of the affected area with separating reflection depth using an optical isolator function.

Figure 2:
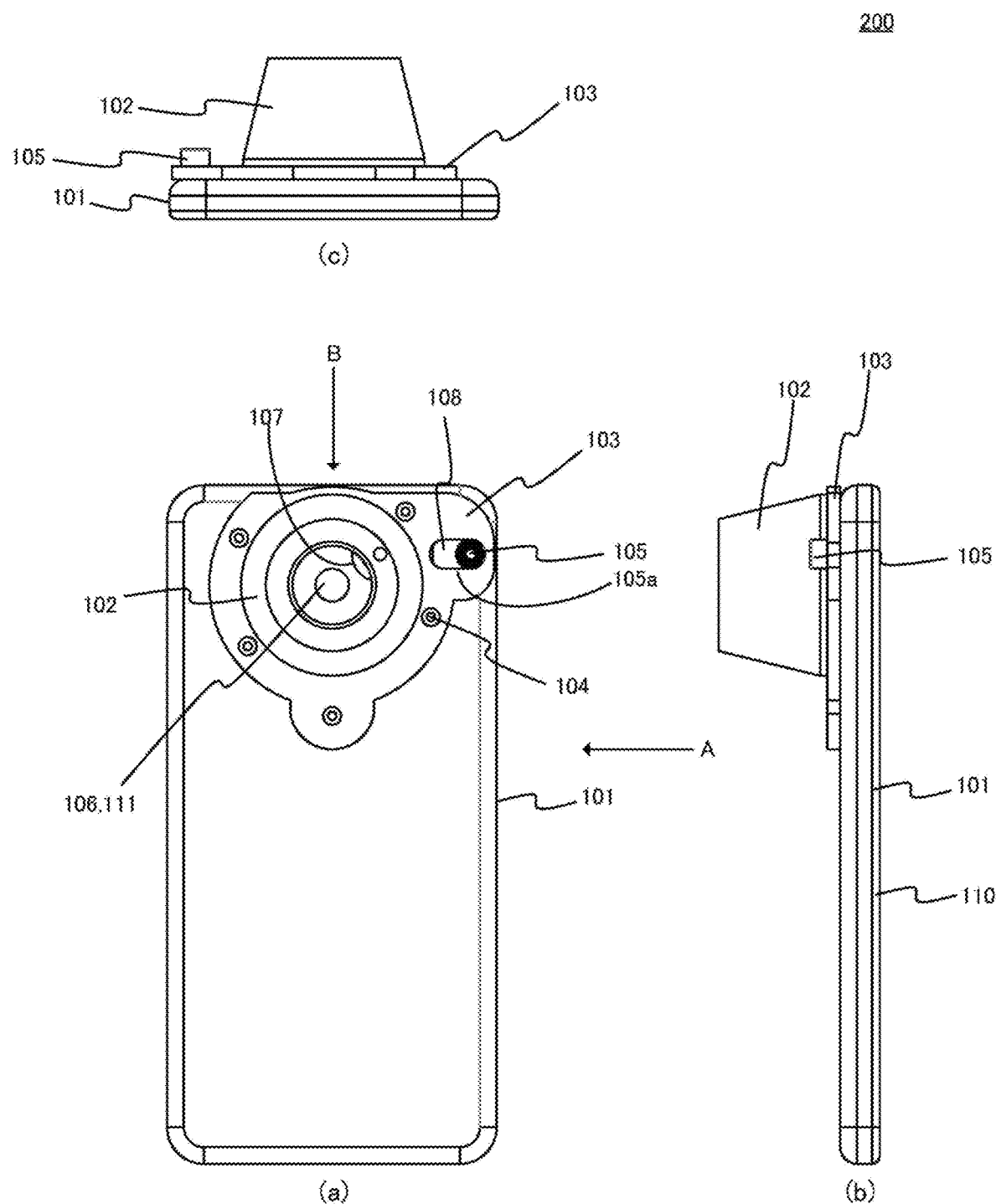
FIG. 2 shows a front view and side views of the dermoscope 100 of the embodiment.

FIG. 2 shows a front view and side views of the dermoscope 100 of the embodiment. FIG. 2(a) shows a front view of the dermoscope 100 of the embodiment, FIG. 2(b) shows a side view, and FIG. 2(c) shows a side view as seen from the direction of the arrow line B. As shown in FIG. 2(a), the base member 103 is fixed to the case 101 with the screw 104, and a circumferentially extended hook is formed on the base member 103. The hook engages with a cavity formed in the internal face of the observation adaptor 102 and detachably retains the observation adaptor 102.

Moreover, in FIG. 2(b), the case 101 has a space on the side opposite to the side where the base member 103 is arranged. The case 101 contains the smartphone 110 within the space with directing the liquid crystal display on the right-hand side of the page, and the camera 111 and the photoflash 17 on the left-hand side on the page.

Furthermore, as shown in FIG. 2(a) and FIG. 2(c), the slider knob 105 is set to have a diameter fitting with the long hole 105a and attached to a second circular polarization filter 108 in the vicinity of the case 101. Moreover, in a position corresponding to the camera of the smartphone in the base member 103, a first circular polarization filter 106 is attached at a position overlapping the camera 111 of the smartphone 110, allowing observation with separating surface reflection from inner reflection of a skin affected area.

Now, a brief description will be made for a principle of observing skin tissue with changing a polarization state in the embodiment. Here, detailed principle would refer to, e.g., JP6705957. A photoflash 107 emits unpolarized LED light, and commonly, unpolarized LED light is irradiated onto skin tissue. The LED light irradiated onto skin tissue reflects to the camera of the smartphone, passes through the first circular polarization filter, and is imaged with an imaging means of the camera such as CCD.

Then, once the slider knob 105 is operated to cover the photoflash 107 with the second circular polarization filter 108, LED light emitted from the photoflash 107 passes through the second circular polarization filter 108, and then is formed into circular polarized light and irradiated onto a skin affected area. In the embodiment, in order to achieve an optical isolator function, the first circular polarization filter 106 and the second circular polarization filter 108 have the same circular polarization characteristics.

When circular polarization filters are used as the first polarization filter 106 and the second polarization filter 108, rays of light reflected on the skin surface have a polarization direction reversed against the circular polarization direction of the second circular polarization filter 108 (translation vectors of light are to be opposite), and thus no longer pass through the first circular polarization filter 106. Meanwhile, reflected light that penetrates to the inside of the skin affected area and is reflected on the deep tissue is to be unpolarized light due to irregular reflection by the inner tissue and the like. Then, since the light goes on to the first circular polarization filter 106 with remaining unpolarized, the first circular polarization filter 106 passes only the reflected light reflected from the deep tissue of skin by providing an optical isolator function and allows photographing by the camera 111 of the smartphone 110.

As explained above, the embodiment allows observation with separating reflection from the skin surface and reflection from the deep tissue of skin, by synergic effect of the first circular polarization filter 106 and the second circular polarization filter 108. Moreover, similar observation is also allowed by cross-Nicol arrangement using linear polarized light used in conventional polarization observation. However, cross-Nicol arrangement of linear polarizers considerably reduces transmissivity and requires to greatly enhance light quantity of irradiated light for performing observation under sufficient brightness and cannot be used in the embodiment. However, in the present disclosure, another embodiment, which the first polarization filter 106 and the second polarization filter 108 are both linear polarization filter and these are used in a cross-Nicol arrangement, is not excluded.

Meanwhile, with use of an optical isolator function as in the embodiment, observation can be performed with separating reflection from the deep part of skin, with the decline nearly as transmissivity of a polarization filter. This allows photographing of an affected area with sufficient brightness under light quantity nearly as that of a photoflash mounted on a smartphone.

The bottom diameter of the observation adaptor 102 of the embodiment is determined so as to contain the camera and the photoflash 107 of a smartphone to be used within such diameter of the bottom. LED light emitted from the photoflash 107 is reflected with the inner wall of the observation adaptor 102 and efficiently irradiated on an affected area, allowing obtaining a brighter affected area image.

Figure 3:
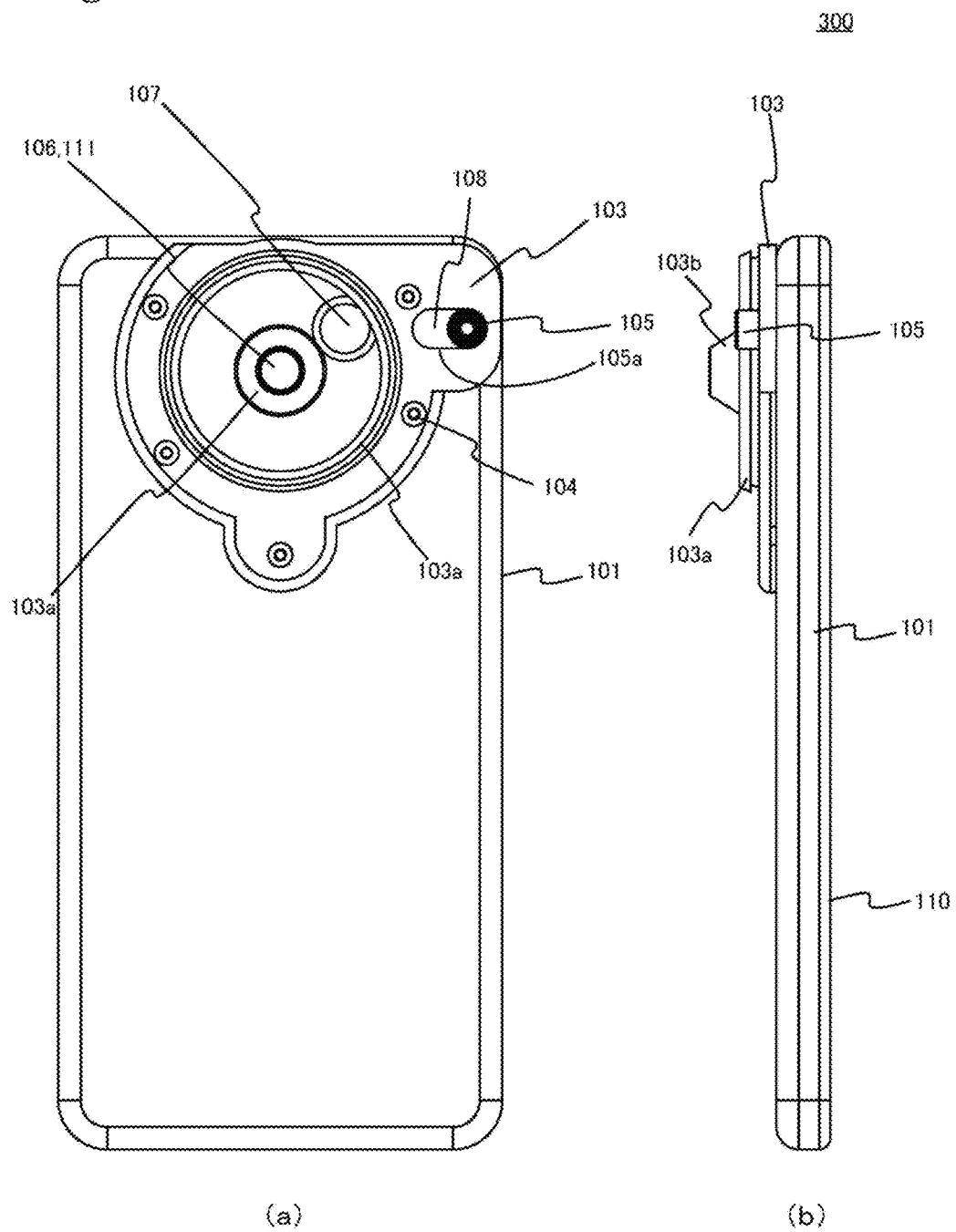
FIG. 3 shows a more detailed configuration of the dermoscope 100 of the embodiment.

FIG. 3 shows a more detailed configuration of the dermoscope 100 of the embodiment. FIG. 3(a) shows a front view, and FIG. 3(b) shows a side view. As shown in FIG. 3(a), the first circular polarization filter 106 is arranged in the base member 103 so as to cover the camera of the smartphone. In addition, in the base member 103, a circular hook 103a to be attached to the observation adaptor 102 is formed, and a protrusion 103b for retaining a close-up lens (not shown) is formed so as to surround the camera 111 of the smartphone 110. The protrusion 103b formed in the embodiment shown in FIG. 3 contains and retains the close-up lens 103c in its inner space, allowing observation with enlarging an affected area to a predetermined magnification. The close-up lens is mounted for performing observation of a close-range object such as skin affected area and can be used that has a focal distance (f value) within 12 mm-25 mm but is not particularly limited.

The slider knob 105 is set to be movable right and left along the long hole 105a; when moved to the left side on the page in FIG. 3(a), it causes the second circular polarization filter 108 to cover the photoflash 107, thereby generating circular polarized light.

FIG. 3(b) shows a side view of the dermoscope 100 of the embodiment and shows a three-dimensional positional relation of the case 101, the base member 103, and the slider knob 105. The base member 103 is screwed to the case 101a with a plurality of screws 104, and detachably fixed. Furthermore, the second circular polarization filter 108 is retained within a gap formed between opposite faces of the base member 103 and the case 101, and controls photo LED light to be unpolarized/circular polarized corresponding to movement of the slider knob 105.

The base member 103 is formed of thermoplastic material such as polystyrene or polypropylene, and is manufactured by, e.g., a 3D printer. In a further embodiment, it can also be manufactured by casting technology using a die according to a conventional method.

Figure 4:
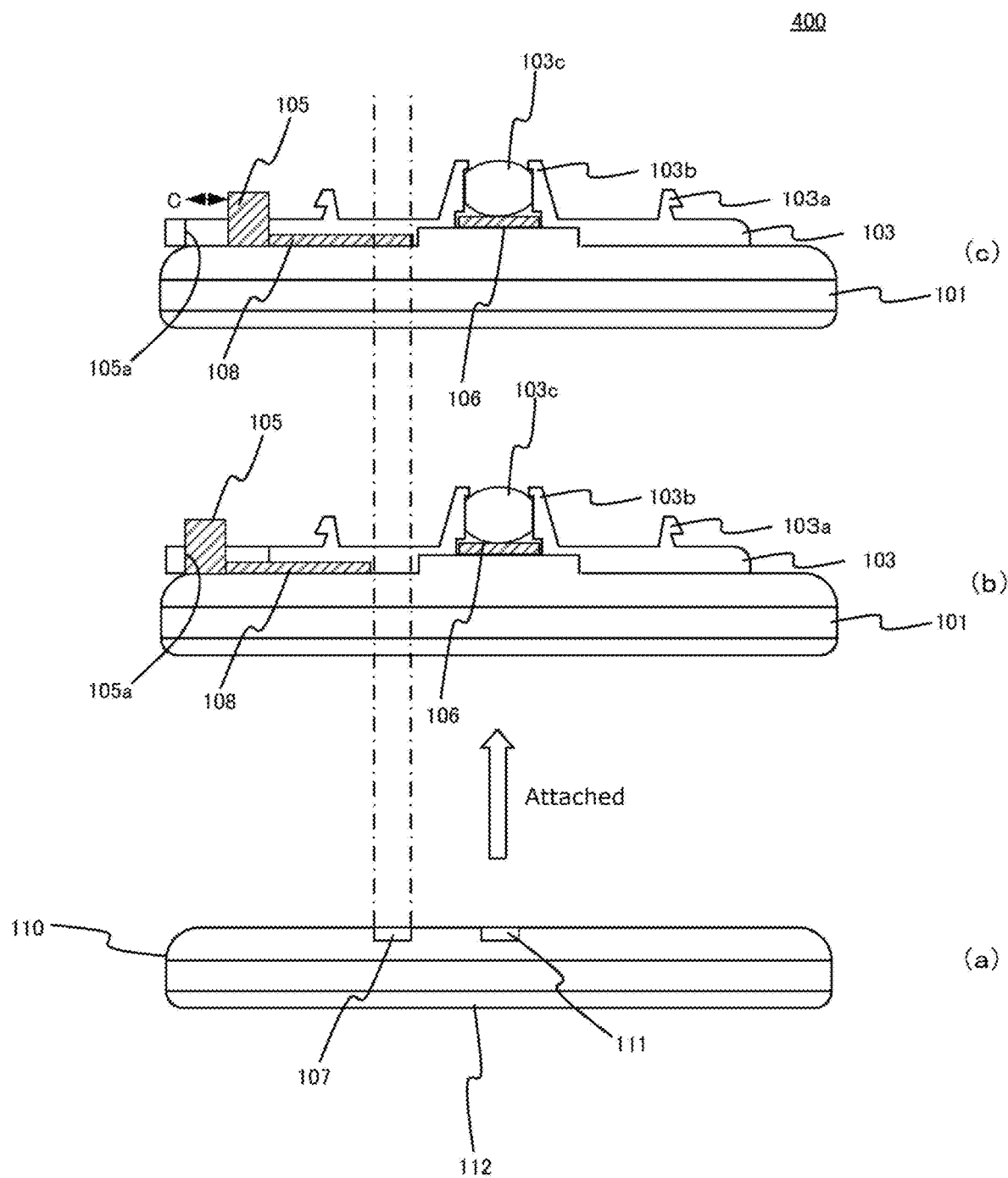
FIG. 4 illustrates a configuration and a polarization adjustment function of the dermoscope 100 of the embodiment.

FIG. 4 illustrates a configuration and a polarization adjustment function of the dermoscope 100 of the embodiment. As shown in FIG. 4(a), the smartphone 110 includes the camera 111 and the photoflash 107 on the back face and has a liquid crystal display 112 disposed opposite to the camera 111. A user (a doctor or patient) can operate the dermoscope 100 with viewing a graphical user interface (GUI) displayed on the liquid crystal display 112.

The dermoscope 100 of the embodiment is configured by retaining the smartphone 110 shown in FIG. 4(a) within the space formed in the case 101 shown in FIG. 4(b). The areas of the photoflash 107 and the camera 111 in the case 101 are cut out so as to correspond to each shape to make a configuration that avoids optical loss. Additionally, as shown in FIG. 4(b), a close-up lens 103c is contained in the space formed by the protrusion 103b. The protrusion 103b also functions as a fixture for fixing a narrow-area observation adaptor 109 or a wide-area photographing adaptor 1410 as described later.

The close-up lens 103c provides a predetermined magnification required for the function of the dermoscope. Now, the smartphone 110 makes it possible to observe with further magnified scale using a pinch-out and the like. Furthermore, by equipping a wide-area photographing adaptor 1410, wide-area images including affected areas such as a hand, leg, planta pedis, and a face are enabled to be photographed.

Moreover, as shown in FIG. 4(b), the slider knob 105 is arranged on the left-hand side on the page in the area of contact of the case 101 and the base member 103, and the second circular polarization filter 108 is attached to the slider knob 105. The second circular polarization filter 108 is movably contained in a space formed between the base member 103 and the case 101. With the slider knob 10 shifted to the left-hand side on the page of the long hole 105a, the second circular polarization filter 108 move aside to a position not interrupting the photoflash 107 along the direction of the long hole. Here, the long hole is not limited to be elliptic, and can be formed in any shape, such as a U-shape, an angled U-shape, or a bent shape, corresponding to arrangement of member components and operability.
[0049]
Furthermore, as shown in FIG. 4(b), the first circular polarization filter 106 is arranged at a position corresponding to the camera 111 of the base member 103, and scattered light by LED light emitted from the photoflash 107 can be observed through the first circular polarization filter 106. Here, the arrangement of the first circular polarization filter 106 is illustrative and can be arranged as any arrangement in the dermoscope 100 as long as rays of light incident to the camera 111 of the smartphone 110 can pass through the first circular polarization filter 106.

Additionally, as shown in FIG. 4(c), the slider knob 105 shifts along the long hole 105a as shown in the arrow C. With the slider knob 105 fully shifted to the right-hand side on the page, the second circular polarization filter 108 is displaced to a position to fully cover the photoflash 107. By contrast, with a full shift to the left-hand side on the page, the photoflash 107 is not covered. Accordingly, displacement of the position of the slider knob 105 allows easy adjustment of polarization state of the photoflash 107.

Here, in a particular embodiment, each contact face of the case 101 side of the slider knob 105 and the case 101 side of the base member 103 is formed as a curved surface having a fitting curvature, thereby also providing improved fixation property of the slider knob 105 along the arrow C.

Figure 5:
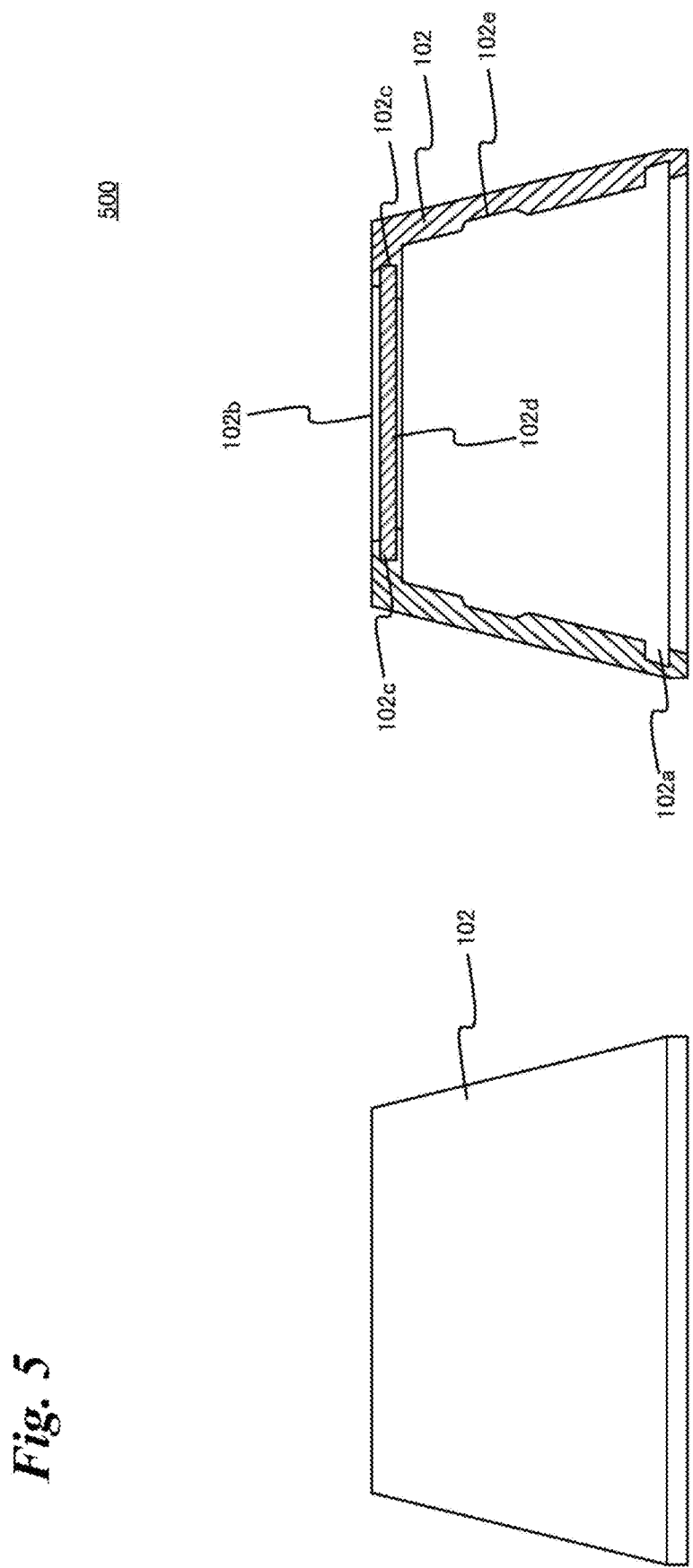
FIG. 5 shows a detailed configuration of an observation adaptor 102 used in the embodiment.

FIG. 5 shows a detailed configuration of an observation adaptor 102 used in the embodiment. As shown in FIG. 5(a), the observation adaptor 102 has a generally truncated cone shape, the bottom face of which is set to a diameter to contain the photoflash 107 and the camera 111 of the smartphone within such bottom face.

FIG. 5(b) shows a cross-section structure of the observation adaptor 102. The observation adaptor 102 has a groove 102a formed on the bottom, in which the groove engages with the circular hook 103a formed in the base member 103. Moreover, the top face has an opening 102b formed thereon, and a circumferential groove 102c formed in the inner periphery of silicone resin formed the top face retains a glass protection member 102d to protect the inside of the observation adaptor 102 from dirt and the like.

Additionally, a space is formed between the top face of the observation adaptor 102 and the protection member 102*d*. The space is set to allow containing gel to spread on an affected area for skin observation and preventing irregular reflection on the skin surface.

The lateral side connecting the bottom face and the top face of the observation adaptor 102 has a close vicinity part 102*e* formed for the purpose of facilitating deformation of the observation adaptor 102. A user grasps the close vicinity part 102*e* of the observation adaptor 102 and deforms the bottom, thereby easily removing the observation adaptor 102 from the base member 103. The observation adaptor 102 thus removed is subjected to sterilization or the like, applied on the base member 103, and then used.

Figure 6:
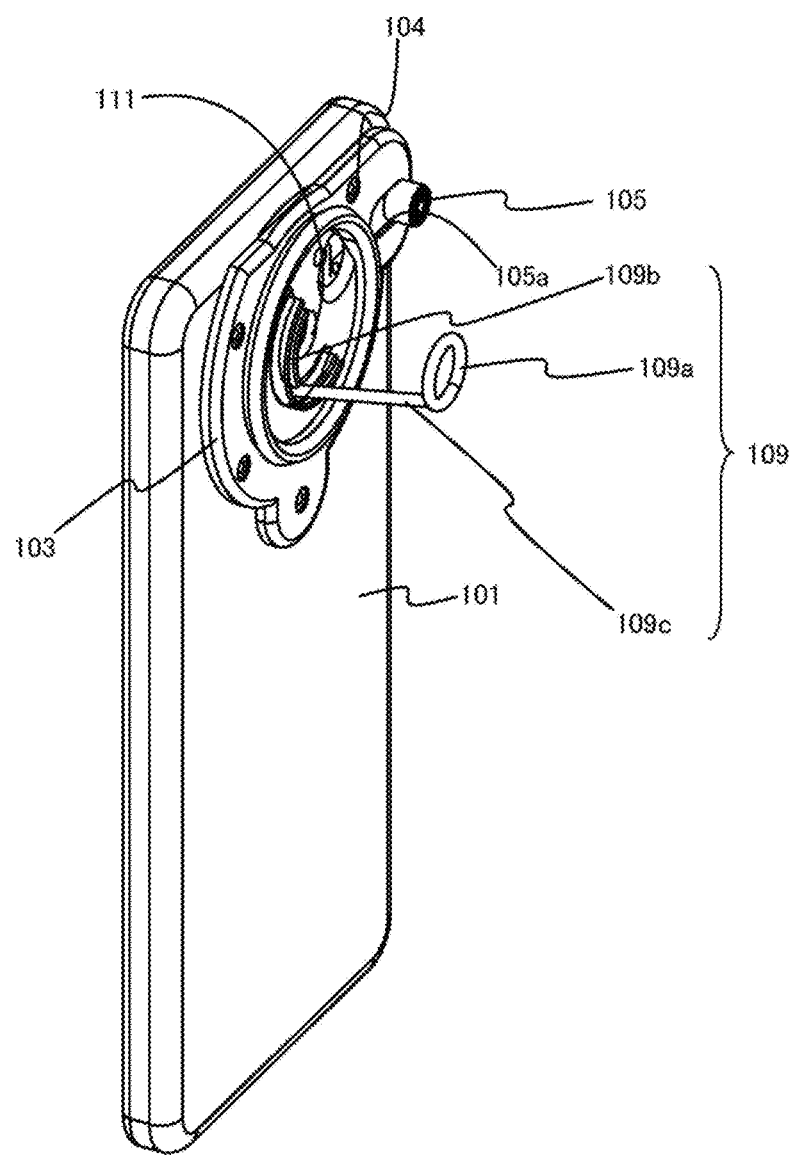
FIG. 6 shows a perspective view of a second embodiment 600 of the dermoscope 100 of the embodiment.

FIG. 6 shows a perspective view of a second embodiment 600 of the dermoscope 100 of the embodiment. The dermoscope 100 of the second embodiment is shown with removing the observation adaptor 102 for explanatory convenience. Here, members and components in common with the first embodiment are shown with the same symbols, and further detailed description is omitted.

Fixation of the base member 103 to the case 101 is as the first embodiment 200. In the second embodiment 600, the protrusion 103*b* surrounding the camera 111 in the base member 103 is not formed and made into a flat form. In the second embodiment, the protrusion 103*b* can be formed with an appropriate size, and the close-up lens 103*c* can be retained. In a further embodiment, the close-up lens 103*c* can also be a plastic lens and fixed with a suitable adhesive.

Meanwhile, in the second embodiment, a stand member 109 is formed on the side to be attached to observation adaptor 102, in the base member 103. The stand member 109 retains a position of the top face of the observation adaptor 102 relative to the smartphone 110, to a certain position. The stand member 109 includes a supportive ring 109*a* for contacting with the inside of the top face of the observation adaptor 102 and retaining the top face to a certain position relative to the smartphone 110; a semicircular base part 109*b* formed in the base member 103; and a supportive bar 109*c* extending between the supportive ring 109*a* and the base part 109*b*. Furthermore, a circular recess 103*d* adapting to the base part 109*b* are formed to the base member 103 for fixing the base part 103*c* such that the base part 109*b* may be snapped into the circular recess 103*c*.

The diameter of the supportive ring 109*a* is set to fit with a space between the opening of the top of the observation adaptor 102 and the inner wall of the observation adaptor 102, thus retaining the top face of the observation adaptor 102 to a certain height. The base part 109*b* is integrally formed as a substantially semicircular projection surrounding the camera 111 of the smartphone 110, on the inner diameter side relative to the hook 103*a* formed in the base member 103.

Additionally, the supportive bar 109*c* is fixed to the base part 109*b* and elongated to the supportive ring 109*a* and extends from the opposite side of the photoflash 107 across the camera 111 so as to avoid interrupting LED light from the photoflash 107.

FIG. 7 shows a front view with removing an observation adaptor 102 in the second embodiment 600 of the dermoscope 100 shown in FIG. 6 (FIG. 7(*a*)) and a detailed configuration of a stand member 109 for providing a function for a narrow-area observation adaptor. As shown in FIG. 7, the base member 103 is formed with a circular recess 103*d* having the semicircular or the arc-shaped base part 109*b* formed inside the hook 103*a*, and the supportive bar 109*c* extends substantially from the opposite side across the camera 111 of the photoflash 107 to the supportive ring 109*a*. The number of the supportive bars 109*c* is not limited to one, and the supportive ring 109*a* can be supported with two, three or more of the supportive bars 109*c* depending on application.

For example, when the stand member 109 has one supportive bar 109*b* is as a single one, it is preferable to a provide observation adaptor to insert into a narrow small part such as the nasal cavity or earhole. Moreover, in setting as two bars, it is preferable in view of improving stability with using thinner members for the supportive bar 109*c*. Further, depending on needs and observability, three or more of the supportive bars 109*c* can be used. Now, all or a part of the supportive bar 109*a* may be covered with a silicone tube to reduce discomfort when contacting around the affected regions.

FIG. 7(*b*) shows the stand member 109 according to one embodiment which provides a function of the narrow-area observation adaptor. Here, when the narrow-area observation adaptor is used shown in FIG. 7(*b*), the circular recess 103*d* for receiving the base part 109*b* may not be formed to the base part 103 and the base part 109*b* may be fixed by an outer periphery of the protrusion 103*b*. Furthermore, according to the present embodiment, the base part 109*b* engages with the protrusion 103*b* formed to the base part 103 to be fixed to the base part 103. The stand member 109 shown in FIG. 7(*b*) functions as the narrow-area observation adaptor and includes a supportive ring 109*a*, base part 109*b* and a supportive rod 109*c* extending between the supportive ring 109*a* and the base part 109*c*. A distance between the base part 109*c* and the supportive ring 109*a* may be a distance which may focus within a predefined magnification of the camera 111. In addition, a diameter of the supportive ring 109*a* may be adopted depending on sizes of narrow-affected area.

Furthermore, the silicone tube 109*d* is equipped to the supportive ring 109*a* such that the discomfort when the supportive ring 109*a* becomes contact to the affected area. The narrow-area observation adaptor shown in FIG. 7(*b*) may be fixed to the outer periphery of the protrusion 103*b* of the base member 103 and then the smartphone 110 is positioned where the supportive ring 109*a* is positioned so that to the affected area becomes within the supportive ring 109*a* to conduct various observation and photographing.

In FIG. 7(*a*), the first circular polarization filter 106 is arranged at a position substantially overlapping the position of the camera 111, thus allowing light from the photoflash 107 to pass through the first circular polarization filter 106 to provide observation. The arrangement described above enables efficient observation without interrupting LED light emitted from the photoflash 107.

Figure 8:
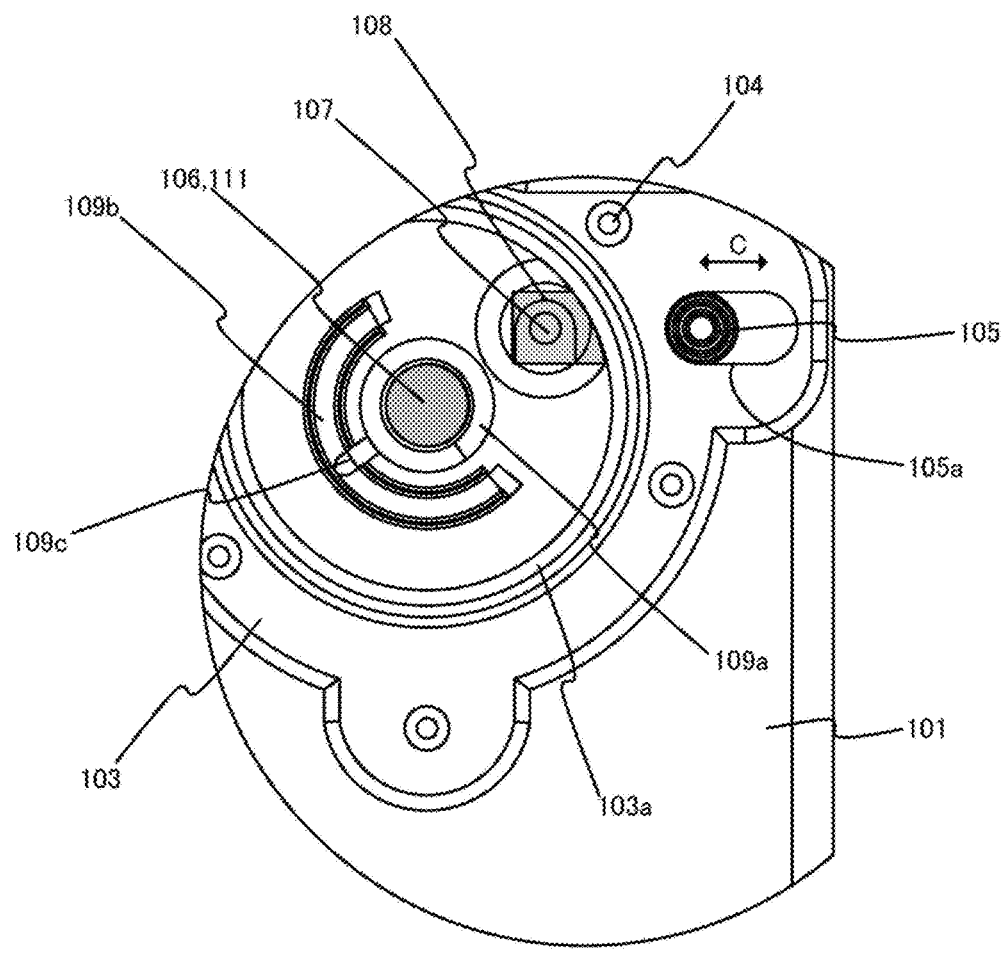
FIG. 8 shows a region of the circle D in FIG. 7 in an enlarged manner.

FIG. 8 shows a region of the circle D in FIG. 7 in an enlarged manner. The dermoscope 100 is formed with containing the smartphone 110 within the case 101, and the base member 103 is fixed to the case 101. The base member 103 has the hook 103*a* formed therein, which can be detachably attached to the observation adaptor 102.

Inside the hook 103*a*, the base part 109*b* of the stand member 109, the supportive ring 109*a*, and supportive bar 109*c* are formed. In addition, according to the embodiment shown in FIG. 8, the first circular polarization filter 106 (shown by hatching) covers the camera 111 and allows the smartphone 110 to obtain an image through the first circular polarization filter 106.

Furthermore, the slider knob 105 is arranged at a part on the right-hand side of the base member 103, and the slider knob 105 slides along the inner wall of the long hole 105*a* in the direction of the arrow C. At a position of shift to the left end of the long hole 105a, the slider knob 105 extends to a position where the second circular polarization filter 108 fully covers the photoflash 107, as shown in in FIG. 7. The slider knob 105 also, upon shifting to the right end of the long hole 105a, moves aside to a position to fully expose the photoflash 107.

In observation with the photoflash 107 being uncovered with the second circular polarization filter 108, observation is made using reflection from the skin surface tissue and the deep tissue. By contrast, in observation with the photoflash 107 being covered with the second circular polarization filter 108, synergistic effect with the first circular polarization filter 106 caused the first circular polarization filter 106 to provide an optical isolator function, thereby allowing observation of an affected area by reflection from the deep tissue of skin.

In the dermoscope 100 having the configuration described above, applying a dermoscope adapter to the smartphone 110 confers a function as a dermoscope on the smartphone. This can improve operability and information-processing capacity with lighter weight relative to a dermoscope using a digital camera as a conventional one.

Moreover, the dermoscope 100 of the embodiment provides an optical isolator function with combined use of first circular polarization filter 106 and the second circular polarization filter 108, thereby enabling provision of a brighter image then that of conventional dermoscopes that perform polariscopy using cross-Nicol arrangement. Moreover, in the dermoscope 100 of the embodiment, inner face reflection of the observation adaptor 102 further leads light efficiently to a skin affected area. Consequently, this allows sufficient observation under light quantity nearly as that of the photoflash 107, which is normally mounted on the smartphone 110. Incidentally, oral surgical use requires a longer focal length of an additional lens such as a close-up lens 103d and may use a physically long observation adaptor 102. In such case, illumination light may possibly be attenuated. In the case of this embodiment, metal evaporation of the inner face of the observation adaptor 102, lamination of white diffuse-reflection sheets, or the like can increase inner face reflection and improve illumination light intensity. Additionally, with the close-up lens 103d having a short focal length, it is also possible to confer a light scattering action on the inner face of the observation adaptor 102 and improve uniformity of illumination light.

Furthermore, since imaging is performed using the smartphone 110, which is capable of higher-performance information processing relative to conventional dermoscopes, troublesome settings such as image processing capacity or observation condition settings can be provided as a smartphone-executable application program, a so-called dedicated app. Consequently, the dermoscope 100 of the embodiment is allowed to perform more highly efficient observation and diagnosis relative to conventional dermoscopes, and also to provide an efficient remote diagnosis using an internet conference system such as ZOOM®, Microsoft Teams®, or Webex®.

The dermoscope 100 of the embodiment can also be used with applying a lightguide to the observation adaptor 102 for observing a narrow small, affected area described in JP6705957, with applying a scale, or the like.

Figure 9:
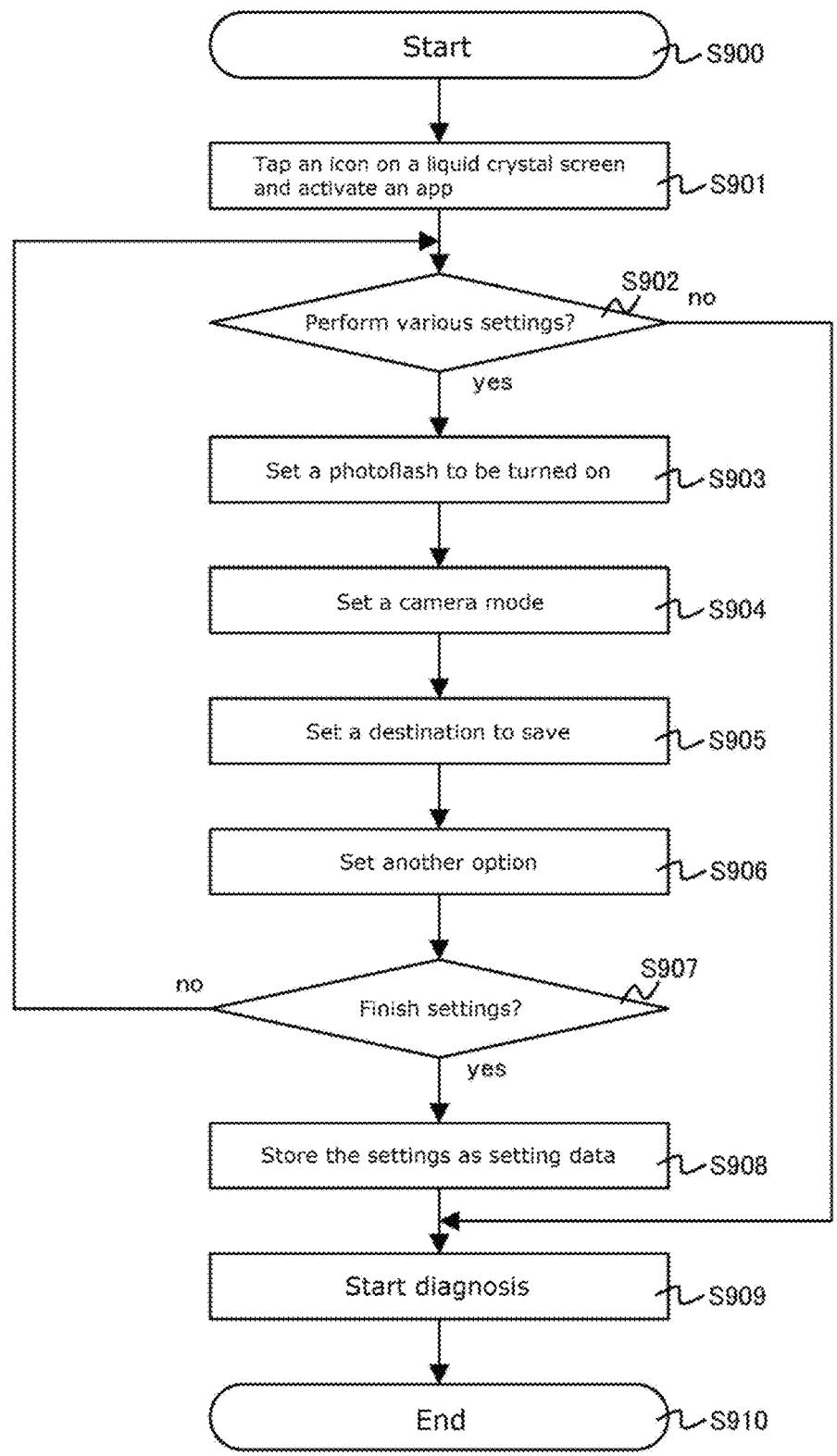
FIG. 9 shows a flowchart illustrating how to use the dermoscope 100 of the embodiment.

Hereinafter, description will be made how to use the dermoscope of the embodiment with reference to FIG. 9 and FIG. 10. FIG. 9 shows a flowchart illustrating how to use the dermoscope 100 of the embodiment. The method in FIG. 9 starts from step S900; and corresponding to activation of the smartphone 110, at step S901, an icon showing an app for using a dermoscope on a liquid crystal display is tapped to activate an observation app. According to the present embodiment, since the optimal mode settings are provided when the observation app is invoked, users may instantly perform the observation and the photographing.

At step S902, various setting buttons displayed as a GUI by the observation app are tapped to inquire whether various settings are to be performed. If a user uses the app for the first time or intends to perform observation with settings different from a conventional manner (yes), tapping of the button forwards the processing to step S903. For example, a setting for turning on the photoflash is made at step S903 (automatic setting by the app may be applied), and a setting of a camera mode such as static photographing or video photographing is made at step 904.

Further another embodiment, for accommodating contrasts to medical uses, the app may provide a button for setting desired γ corrections and an adjustment button of ISO sensitivity. Further in another embodiment, the app may provide a switching button of a white balance between a vivid-mode, in which the vivid-mode may display a flesh color clearly with displaying images under wider-color reproduction range by setting color balance of displayed images based on the white of LED as the illumination light and a mode of the white correction (i.e., auto-white mode), in which the white correction is performed by setting the sum of entire chromaticity as the white. In further another embodiment, when each of dark regions and light regions are present at the same time, a button for instructing an HDR (High Dynamic Range) photographing mode so that both the dark regions and the light regions may be displayed without degrading the contrasts.

Once the setting of the camera mode is finished, the destination to save is set at step S905, e.g., a setting whether to store in a built-in RAM or to store in an external storage medium such as an SD card is made. Furthermore, the photographed data may be adequately updated to a network-storage means such as Dropbox (trademark) and may be transferred to a computer recording electronic-clinical records and then may be deleted from the SD card. Then, if a setting of photographing magnification or another optional setting is needed, such setting is made at step S906.

After all the settings are finished, step S907 determines whether all setting items has been set up. If the content of alteration needs to be changed (no), tapping a button displayed on the liquid crystal display, such as "Change settings", causes the processing to return to step S902, thus allowing reconfiguration.

By contrast, if the settings are completed at step S907, tapping a button displayed on the liquid crystal display, such as "Finish settings", instructs the app to finish the settings (yes); and at step S908, the information of the setting items is stored as setting data in a nonvolatile memory such as a flash memory. The setting data thus stored is made available for subsequent observation, and preparation is completed for automatically activating a camera function of the smartphone 110 and starting observation based on the preset conditions.

Then, using the dermoscope of the embodiment, a user starts observation of an affected area in a patient with a direct mode (a mode with use of only the first circular polarization filter 106) and a polarization mode (a mode with use of the first and second circular polarization filters 106 and 108) at step S908. At that time, the user performs enlargement, photographing (video, static image), storage, transmission using an internet conference system, and the like, if needed.

At step S910, after completion of the observation, the observation app is finished to end the processing in FIG. 9. The static image or video thus shot is loaded into a personal computer and stored in association with a patient name and the like, if required. Such information may be edited as an electronic medical chart.

The dermoscope 100 of the embodiment employs a smartphone, which is for general purpose and allows higher-performance information processing unlike imaging apparatuses capable of operating a camera-dedicated application such as a digital camera, and the troublesome settings as described above can thus also be performed easily by a GUI function. The dermoscope 100 of the embodiment can also easily control processing, such as save or alteration of magnification, via a GUI function, thus allowing efficient observation or diagnosis.

Figure 10:
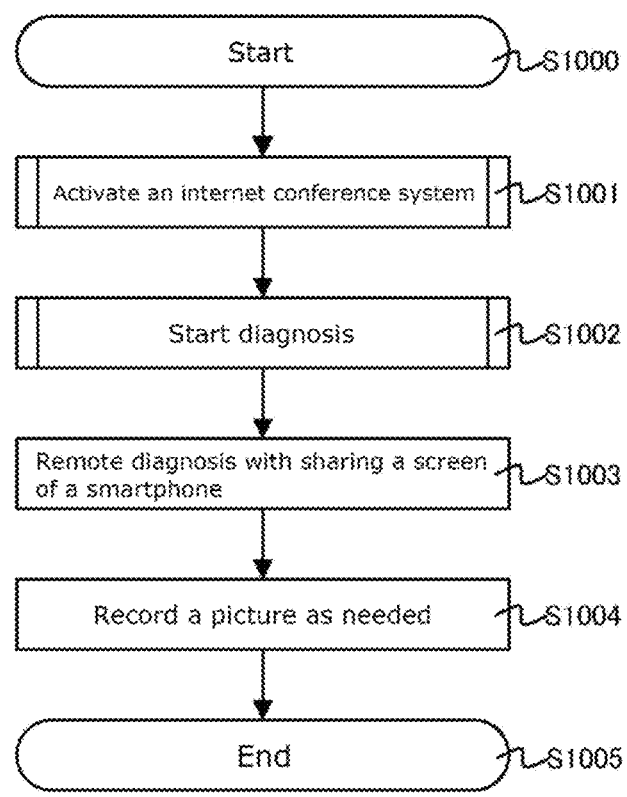
FIG. 10 shows a flowchart of processing of remote diagnosis using the dermoscope 100 of the embodiment.

FIG. 10 shows a flowchart of processing of remote diagnosis using the dermoscope 100 of the embodiment. The processing in FIG. 9 starts from step S1000, and an internet conference system is activated at step S1001. The internet conference system can be used with any application previously known and can also be utilized with another application that provides the same function.

At step S1002, the observation app is activated to start diagnosis. Here, use of a display sharing function in the internet conference system enables sharing an image with a doctor who performs diagnosis in a remote location.

At step S1003, a display of the smartphone is shared with use of the display sharing function of the internet conference system, thereby performing remote diagnosis. In image capturing for the remote diagnosis, a patient can capture an image by him/herself, allowing diagnosis remotely. The remote diagnosis also includes the case, for example, where a non-specialist physician in a local region sends an image to a specialist physician in a university hospital or the like and asks for remote diagnosis. Furthermore, these diagnostic results can also be recorded and reserved as a video image at step S1004.

Incidentally, in use of an internet conference system, an internet communication facility mounted on the smartphone 110 can be used such as a Wi-Fi facility, a next-generation wireless communication standard such as 4G or 5G, Bluetooth®, or Ethernet®. Additionally, in wireless communication, security of communication can be improved using a communication method with use of an encryption key such as WEA or WEP, or others, e.g., quantum cryptography.

At the time when the diagnosis is ended, the internet conference system and the observation app are terminated to finish the remote diagnosis.

As described above, the dermoscope 100 of the embodiment enables efficiently performing remote diagnosis, thereby allowing improving quality of medical care in remote rural areas.

Figure 11:
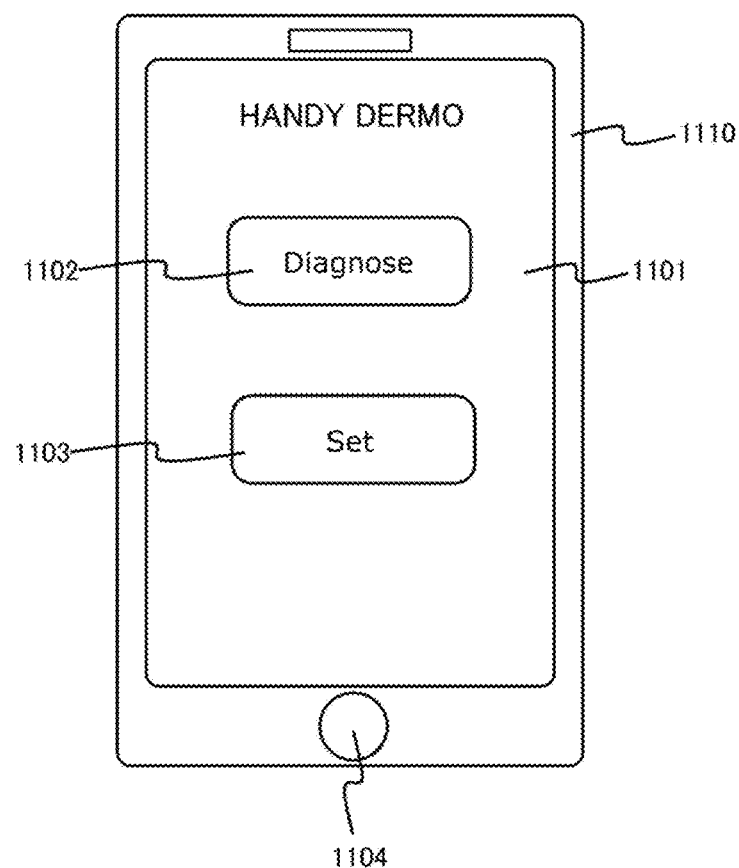
FIG. 11 shows an embodiment of a GUI 1100 displayed by an observation app that controls the dermoscope 100 of the embodiment.

FIG. 11 shows an embodiment of a GUI 1100 displayed by an observation app that controls the dermoscope 100 of the embodiment. The smartphone 1110 shown in FIG. 11 is applied to the dermoscope adapter of the embodiment, and the backside of the page of FIG. 11 retains the observation adaptor 102 and the like. Once the user selects and taps an icon of the observation app displayed on a liquid crystal display 1101 of the smartphone 1110, the observation app is activated and displays the display in FIG. 11.

When the user intends to perform various settings, tapping a "Set" button 1103 starts the processes below step S902 in the processing in FIG. 9. Meanwhile, tapping a "Diagnose" button 1102 by the user starts the processing of step S909 in FIG. 9. Here, the user intends to receive remote diagnosis, activation of an internet conference app and display sharing in advance or after tapping the "Diagnose" button 1102 in the processing in FIG. 11 promptly enables remote diagnosis without performing complicated operation. Additionally, use of a programmed start function of an internet conference system allows remote diagnosis to automatically start with the beginning of the diagnosis.

When the user wants to finish the diagnosis, touching a home button 1104 terminates the observation app and the internet conference app. Moreover, in remote diagnosis, voice calls can also be done as needed, thus allowing efficient observation and diagnosis.

Figure 12:
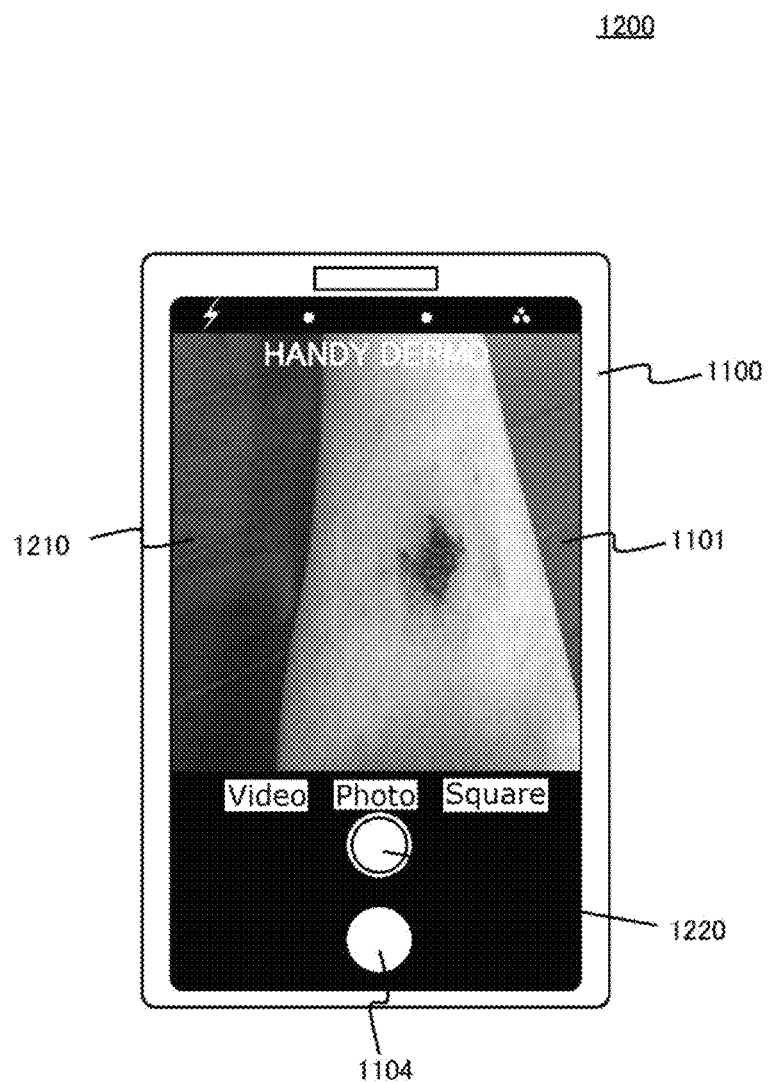
FIG. 12 shows an embodiment to observe an affected area using the dermoscope 100 of the embodiment.

FIG. 12 shows an embodiment to observe an affected area using the dermoscope 100 of the embodiment. As shown in FIG. 12, upon activation of the observation app from the smartphone 1110 and tapping of the "Diagnose" button 1102, a camera function is promptly activated with the preset condition settings, for example, in photoflash-on, at magnification of 10, and in the vivid-mode setting. At this stage, the conditions such as a preset magnification, mode of photographing, and save location have been set up, and thus the user can promptly perform observation without any troublesome setting.

The user can perform a pinch-out or pinch-in operation from a liquid crystal display 1101 with watching an affected area 1210 displayed on the liquid crystal display 1101, thereby enlarging or shrinking an image. Then, a shutter button 1220 displayed on the liquid crystal display 1101 is tapped, thereby saving the static image or video thus shot in a specified save location. Moreover, after the end of the observation and diagnosis, touch on the home button 1104 allows efficient termination of the diagnosis.

Figure 13:
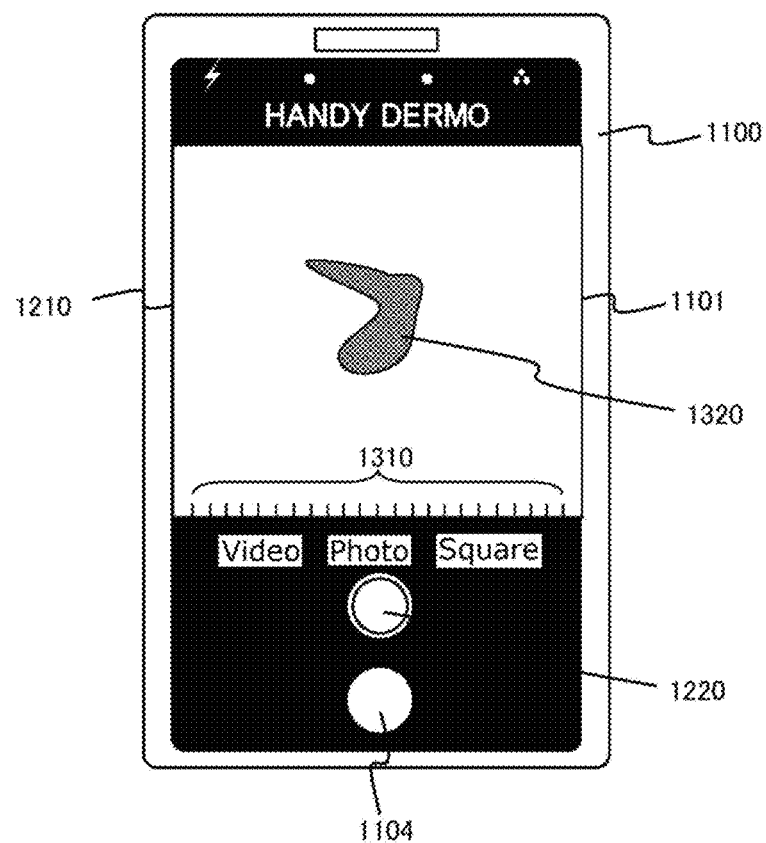
FIG. 13 shows a drawing an embodiment 1300 for displaying the scale display of the present embodiment on the liquid crystal display 1101 of the smartphone 1110 together with the affected-area image rather than fixing on the observation adaptor 102.

FIG. 13 shows a drawing an embodiment 1300 for displaying the scale display of the present embodiment on the liquid crystal display 1101 of the smartphone 1110 together with the affected-area image rather than fixing on the observation adaptor 102. Now, the functional parts commonly described in FIG. 12 are indicated by the same signs and detailed description will be omitted. On the liquid crystal display 1101 of the smartphone 1110, the scale 1310 is displayed by operation of the app and the scale 1310 may be generated by the app with an adequate spacing such as 1 mm width, 0.1 mm width and the like while being displayed on the liquid crystal display 1101 with overlaying to the image data. The user may know the size of the affected area by comparing the scale 1310 and the image of the affected area 1320 displayed on the liquid crystal display 1101. In addition, the scale 1310 may be displayed with adjusted contraction scales corresponding to enlargement and contraction on the liquid crystal display 1101 such that exact measurements may be enabled independently from any contraction scale.

FIG. 14 shows a drawing illustrating an embodiment 1400 equipping a wide area photographing adaptor 1410 for photographing the wider area. FIG. 14(a) shows a side view in the case where the wide area photographing adaptor 1410 is equipped and FIG. 14(b) shows an enlarged perspective view of the wide area photographing adaptor 1410.

The wide area observation adaptor 1410 may be equipped on the dermoscope 100 when one want to record or observe globally depending on requests from physicians where the affected area resides which locations of the body such as a hand, a leg, and a face. The wide area observation adaptor 1410 is formed by fixing a concave lens in a case having almost cylindrical shape: the concave lens 1410b is fixed at the top; and a circular protrusion 1410c is formed at the bottom for making mounting/unmounting of the case easy. A magnification ratio may be set by the distance between the close-up lens 103c and the concave lens 1410b as well as magnification ratio of each of lenses so as to be adequately set depending on usage of wide-area images.

A shown in FIG. 14(b), the wide area photographing adaptor 1410 is composed of two cylindrical parts; the concave lens 1410b is fitted in the upper cylindrical part; and the concave lens 1410b is fixed by the lower cylindrical part when it is fixed to the upper cylindrical part. FIG. 14(b) shows a border by a sign 1410d between the upper cylindrical part and the lower cylindrical part. The wide area observation adaptor 1410 shown in FIG. 14(b) may be fixed by removing the observation adaptor 102, or the stand member 109, or the narrow-area observation adaptor and then fitting the case into the protrusion 103b.

In this condition and by facing the dermoscope 100 to the affected area the affected area within the wide range may be observed. Besides, when the case where the scale 1310 is overlayed on the images, the scale may be displayed after contracting or magnifying to an adequate size.

In addition, photographs taken by the dermoscope 100 of the present embodiment may be sent to a image diagnosis system composed from a server and network storage. In this case, the image diagnosis system may implement a learning phase for associating diagnosis results with images by performing machine learning such as deep leaning using the accumulated sent images and the diagnosis results and then classifying the images foe every diagnosis results.

The image diagnosis system may perform analyses for the images after completion of learning by using the results of the machine learning and the results of the diagnosis such as disease name and so on to the sent image may return the sender such that the diagnosis results may be displayed via. the app. The dermoscope 100 of the present embodiment may take photographs of various lesions as well as having a high image resolution so that higher precision reaching data may be accumulated more efficiently.

Furthermore, the LED for the photoflash of the smartphone may not be white and may be an LED emitting adequate wavelengths form ultraviolet to infrared, and ultraviolet LEDs, red LEDs, and white LEDs may be disposed adjustably in their positions. In this embodiment, diagnoses for boat bug, porphyria as well as melanoma may become possible.

Although the present invention has been described with reference to the embodiments shown in the drawings so far, the present invention is not limited to the embodiments shown in the drawings and can be changed within the range where one skilled in the art can contemplate, with another embodiment, addition, alteration, deletion, or the like. Any aspect falls within the present invention as long as it has an action or effect of the present invention.

INDUSTRIAL APPLICABILITY

According to the present invention, a high-sensitivity and easy-handling dermoscope using a smartphone may be provided.

DESCRIPTION OF SIGNS AND NUMERAL

10: slider knob,
17: photoflash,
100: dermoscope,
101: case,
101a: case,
102: observation adaptor,
102d: protection member,
103: base member,
103a: book,
103b: protrusion
103c: close-up lens
105: slider knob,
105a: long hole,
106: first circular polarization filter,
107: photoflash,
108: second circular polarization filter,
109: stand member,
109a: supportive ring,
109b: base part,
109c: supportive bar,
110: smartphone,
111: camera.

The invention claimed is:

1. A dermoscope for observing skin tissue, the dermoscope comprising:
   a smartphone comprising a camera and a photoflash and being communicable, and being capable of instructing from a graphical user interface displayed on a display of the smartphone,
   a case containing the smartphone and comprising a base member fixed on a side opposite to the display to operate the smartphone, and
   an observation adaptor detachably retained on the base member,
   wherein the camera performs photographing through a first circular polarization filter, and
   wherein the base member movably retains a second circular polarization filter for leading a polarization state of LED light emitted by the photoflash to form circularly polarized light.

2. The dermoscope according to claim 1, wherein the dermoscope comprises a slider knob for adjusting the position of the second circular polarization filter, wherein the slider knob is movably retained along a long hole formed in the base member, and wherein the second circular polarization filter is fixed to the slider knob.

3. The dermoscope according to claim 1, wherein the smartphone enables to display an image of the skin tissue and a scale for measuring a size of an affected area of the skin tissue on the display.

4. The dermoscope according to claim 1, wherein the dermoscope comprises a narrow-area observation adaptor, the narrow-area observation adaptor comprising a stand member including a supportive ring, a base part positioned around a periphery of the camera, and a supportive rod extending between the supportive ring and the base part, wherein the narrow-area observation adaptor is detachable to the base member.

5. The dermoscope according to claim 1, wherein the dermoscope enables to equip an observation adaptor having a truncated-cone shape for observing the skin tissue.

6. A dermoscope adapter comprising a camera and a photoflash and being communicable, and for making a smartphone functioned as a dermoscope, the smartphone being capable of instructing from a graphical user interface displayed on a display of the smartphone, the dermoscope adapter comprising:
   a case comprising a space capable of containing a smartphone, a base member fixed on the case and having formation of a circular hook for retaining an observation adaptor, and the dermoscope adapter containing:

a first circular polarization filter arranged over the camera, and a second circular polarization filter attached to a slider knob movably retained along a long hole formed in the base member, the second circular polarization filter being to extend to the position of the photoflash along with movement of the slider knob.

7. The dermoscope of claim 6, wherein the base member allows equipment of an observation adaptor for observing the skin tissue or a narrow-area observation adaptor for observing a narrow affected area.

8. An application program product comprising a camera and photoflash and being communicable, and a memory storing a program for making a smartphone functioned as the dermoscope according to claim 1, the smartphone being capable of instructing from a graphical user interface displayed on a display of the smartphone, the application program making the smartphone functioned as:

means adapted to make a setting for providing a function as a dermoscope in response to activation of the application program, means adapted to store the setting as setting data in a nonvolatile memory of the smartphone, and means adapted to drive the camera of the smartphone on the basis of the setting data, and to perform at least one function of observation, photographing, and image saving of a skin affected area.

9. The application program product according to claim 8, wherein the smartphone is further functioned as means adapted to send via internet the image taken by the camera and performing remote diagnosis.

10. The application program product according to claim 8, wherein the application program functions the smartphone to display an image of the skin tissue and a scale for measuring a size of an affected area of the skin tissue on the display.

* * * * *